(12) United States Patent
Whitfield

(10) Patent No.: US 10,894,154 B2
(45) Date of Patent: Jan. 19, 2021

(54) IV-LINE END CAP AND SUPPORT

(71) Applicant: Jonathan D. Whitfield, Anderson, SC (US)

(72) Inventor: Jonathan D. Whitfield, Anderson, SC (US)

(*) Notice: Subject to any disclaimer, the term of this patent is extended or adjusted under 35 U.S.C. 154(b) by 0 days.

(21) Appl. No.: 16/148,290

(22) Filed: Oct. 1, 2018

(65) Prior Publication Data

US 2019/0030313 A1 Jan. 31, 2019

Related U.S. Application Data

(63) Continuation-in-part of application No. 15/281,890, filed on Sep. 30, 2016, now abandoned.

(60) Provisional application No. 62/235,749, filed on Oct. 1, 2015.

(51) Int. Cl.
| | | |
|---|---|---|
| *A61M 39/20* | (2006.01) | |
| *A61M 39/16* | (2006.01) | |
| *A61M 39/10* | (2006.01) | |
| *A61M 5/14*  | (2006.01) | |

(52) U.S. Cl.
CPC .......... *A61M 39/20* (2013.01); *A61M 5/1415* (2013.01); *A61M 39/1011* (2013.01); *A61M 39/162* (2013.01); *A61M 2205/273* (2013.01); *A61M 2209/06* (2013.01)

(58) Field of Classification Search
CPC .......... A61M 39/1011; A61M 39/16; A61M 39/162; A61M 39/165; A61M 39/18; A61M 39/20; A61M 2039/1083; A61M 2039/1088; A61M 2039/1066; A61M 2039/0288; A61M 2039/0285; A61M 2209/06; A61M 2205/273; A61M 5/1415; A61L 2202/24
See application file for complete search history.

(56) References Cited

U.S. PATENT DOCUMENTS

| | | | |
|---|---|---|---|
| 4,667,837 A | 5/1987 | Vitello et al. | |
| 4,921,199 A | 5/1990 | Villaveces | |
| 8,282,046 B2 | 10/2012 | Harding et al. | |
| 8,353,869 B2 * | 1/2013 | Ranalletta | A61M 5/50 604/111 |
| 8,419,713 B1 | 4/2013 | Solomon et al. | |
| 8,430,859 B2 | 4/2013 | McConnell | |
| 8,641,681 B2 | 2/2014 | Solomon et al. | |
| 8,834,650 B2 | 9/2014 | Rogers et al. | |
| 9,527,660 B2 | 12/2016 | Tennican | |
| 9,592,375 B2 | 3/2017 | Tennican | |
| 2005/0230961 A1 | 10/2005 | Walley | |
| 2012/0216359 A1 | 8/2012 | Rogers et al. | |
| 2013/0178804 A1 | 7/2013 | Tennican | |

\* cited by examiner

*Primary Examiner* — Allan D Stevens
(74) *Attorney, Agent, or Firm* — Kim and Lahey Law Firm, LLC; Douglas W. Kim; Seann P. Lahey

(57) ABSTRACT

This invention is directed to a sterile IV tube end cap including a housing attached to a panel; an end cap received in the housing and removably attached to the panel; so that when the IV-line end is attached to the end cap, the end cap cannot be removed from the IV-line end without removing the end cap from the housing. The end cap can receive the IV-line end wherein at least a portion of the IV-line end is received in the housing and the IV-line is secured to the panel so that the IV-line is supported by the panel, end cap, and/or housing.

10 Claims, 9 Drawing Sheets

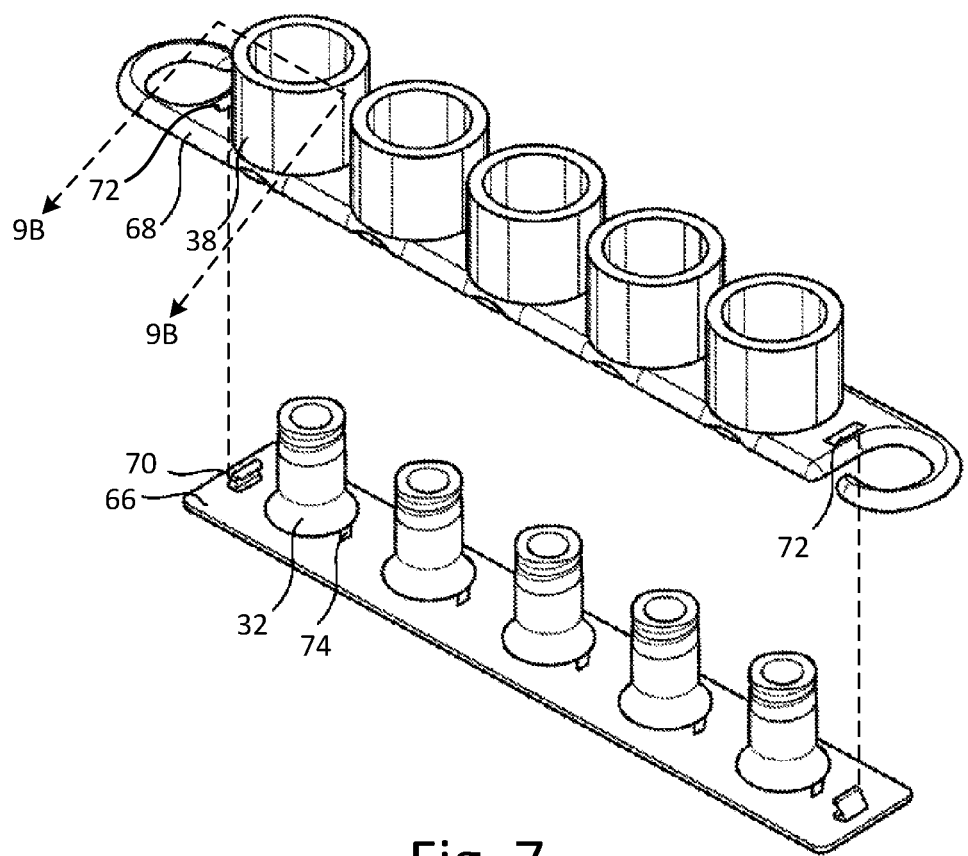
Fig. 7
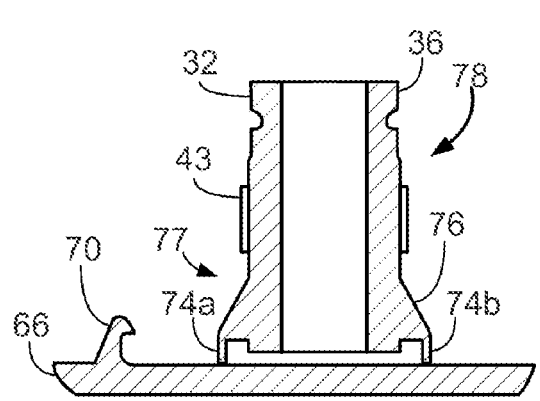
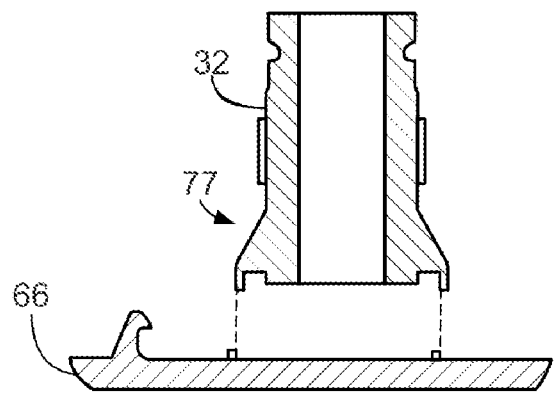
Fig. 8A          Fig. 8B

IV-LINE END CAP AND SUPPORT

BACKGROUND OF THE INVENTION

1) Field of the Invention

The present invention relates to a sterile IV tube end cap that is used to prevent contamination of the IV tube and improve nurse compliance with IV use procedures.

2) Description of Related Art

In the medical field, there is an area coined intravenous ("IV") therapy. IV therapy can be administered through both peripheral and central line sites and are of great interest to the healthcare industry. Typically, the IV needle is inserted into the patient. The IV needle can include a female luer connection. The IV tube can include a male connection that is connected to the IV needle on one end and fluid source or other object at the other end. One challenge with IV therapy lies with potential infections related to peripheral and central IV therapy medical devices that can promote problems at injection sites, or within the lines of medication administration. Such complications are directly reflected in hospital grading and insurance reimbursement, specifically, the central line associated blood stream infections (CLABSIs) and instances of sepsis. This problem can occur when the male end of the IV tube comes in contact with a non-sterile surface, fluid, or solid and is then attached to the needle.

Attempts to reduce these complications include devices and care procedures that have been created to help prevent the contamination of IV-lines. For example, procedures have been put in place where nurses use individually packaged swabs of alcohol to scrub female IV port (or "hub") connectors to disinfect them prior to connecting a male fitting syringe or male luer lock fitting in order to infuse medication through an IV site. Such attempts at covering or cleaning the connectors include U.S. Pat. No. 8,419,713 directed to an assembly for mounting medical connector caps includes a carrier formed from a sheet of material; US Application Publication 2012/0216359 directed to cleaning system for medical implements includes a number of cleaning caps attached to a substrate; U.S. Pat. No. 8,834,650 directed to a system for cleaning a site of a medical implement; and U.S. Pat. No. 8,641,681 directed to disinfecting caps that can be used to cover and disinfect a male luer post of a medical connector. However, none of these attempts provide an assembly for securely holding the connector and preventing contamination of the connector in the first place.

In attempt include seeking to prevent tampering with the contents of a device such as a syringe, U.S. Pat. No. 4,667,837 discloses a ring member disposed about a portion of the stop member and in the sleeve member. The sleeve member can be released from the stop member so that when the sleeve member is released, it can indicate that the syringe has been tampered with. However, nothing in this reference discloses, teaches, or suggests that the stop is one-time use and cannot be replaced into the sleeve.

Devices such as sterile luer lock caps are used to protect both male and female ends of luer lock IV sets. Some caps (like the CUROS® cap) have instilled a form of disinfecting agent, such as isopropyl alcohol, within both male and female caps to provide further assurance that these surfaces are free from germs; however, these attempts to provide a solution do not correctly identify or remedy the actual source of the problem. Assisting nurses to comply with IV capping procedures is the task at hand, as prior devices are not beneficial if nurses do not consistently use them or use them improperly. Without compliance to procedures designed to keep the open male and/or female ends of IV sets free from contaminants, previous devices have not served any purpose at all.

In practice, nurses can fail to follow procedures by: simply not applying sterile caps to the open ends of IV-lines (primary and/or secondary); "looping" the open male end of the line back and connecting it into a female port or end of itself, to create a circle that makes it much easier to manage by then being able to hang from an IV pole or other hanger device; capping the end of the line correctly, only to have it fall to the floor in an attempt to somehow balance the line over the IV pump itself or within the hooks of an IV pole or other hanger to make the line more manageable and secure from falls. Nurses must choose to replace dropped lines (safe practice), or continue using them with possible contamination. Even with a capped line, allowing it to come into contact with the floor increases the risk for infection to enter the blood stream through the IV site.

Additionally, balancing the end of the line somewhere over a pump or IV stand also makes the reuse of the line an inconvenience as one tries to find the end of the line and avoid having it come in contact with the floor, at which point the entire IV-line would need replacement. The above did not mention the time it takes to replace entire IV sets, nor the time wasted untangling multiple lines hanging from IV poles. Sorting and managing multiple IV medications with dangling lines can be a nuisance for nurses dealing with complex patients being treated with multiple IV drugs or solutions and can even potentiate medication administration mistakes.

First, the numerous individual caps placed over male connectors each instance the line is disconnected is time consuming to unpackage, and leaves nurses with more waste to place in receptacles, which also becomes a roadblock to compliance for the end-user. Caps that are attached to a "strip" hanging from IV poles that can be easily peeled off and applied are much more user friendly, and less time consuming to use, which can help increase nurse "correct capping compliance." These detachable male caps produce less waste and are more readily available; however, they still do not solve the glaring problem of nurse compliance and complete ease and willingness of use. Individual, loose cap pieces (even when peeled from a hanging strip) still leaves the nurse searching for a place to balance the male ends of IV-lines over pole hooks or IV pumps, etc., to make them easily accessible each time the line is needed, and leaves many lines dangling to the hospital floor, a breeding ground for infection. And the caps, once removed, are many times placed on the tops of IV pumps or on a nearby surface and reused when the line is again unhooked from the patient.

There is a need for a solution that reduces the tangled IV-lines, prevents sterile lines from falling to the floor, helps insure that nurses will only use a cap once per disconnect, and reduce the need for a nurse to "loop" an IV-line back into itself to create a hanger to make a line more accessible.

Therefore, it is an object of the present invention to provide a medical device directed for simplifying the process for medical professionals to follow the correct procedure when securing and capping the male end of an IV-line.

It is another object of the present invention to provide an assembly that secures the connector to reduce or prevent contamination.

It is another object of the present invention to provide a "one time use" assembly to further reduce or prevent contamination.

SUMMARY OF THE INVENTION

The above objectives are accomplished according to the present invention by providing an IV-line end cap and support comprising: a rear panel having an end cap attached to the rear panel by a breakaway connection; a base included in the end cap having a diameter larger than the diameter of a proximal end of the end cap; an end cap rotation stop disposed on an outer wall of the end cap; a circumferential flange included in the end cap configured to engage with an IV-line end securing the end cap to the IV-line end; a front panel attached to the rear panel having a hook; a housing attached to the front panel having a bore extending through the housing and rear panel and configured to receive the end cap through an entry opening; a housing rotation stop disposed on an inner wall of the housing and configured to prevent the end cap from rotating in a first direction; wherein the end cap, breakaway connection, and housing are configured to allow the end cap to freely rotate within the housing preventing IV-line from being removed from the end cap until the end cap is removed from the housing through an exit opening; an insert stop included in the housing configured to cooperate with the base of the end cap and prevent the end cap from being reinserted into the housing; a sterilization pad included in a control opening defined in the end cap carrying a sterilization agent and, a tab removably attached to an open end of the housing configured to cover the housing prior to the IV-line end being attached to the end cap.

The insert stop can be a flap and can be configured to deform when the end cap is removed from the housing. The housing rotation stop is configured to deform when the end cap is removed from the housing.

The invention can include a sterile IV tube end cap comprising: a housing attached to a strip; an end cap received in the housing and removably attached to the strip; a housing sloped portion or rotation stop defined on an inner wall of the housing; an end cap sloped portion or rotation stop cooperatively associated with the housing sloped portion so that when the IV tube is attached to the end cap, the IV tube cannot be removed from the end cap without removing the end cap from the strip; a first fastening member for removably attaching the end cap to the strip; and, whereas the end cap receives the male end of an IV tube wherein a portion of the IV tube is received in the housing and the IV tube is secured to the strip so that the IV tube cannot be removed from the end cap without removing the end cap from the strip. The invention can include a second fastening member for receiving the first fastening member and securing the housing to the strip.

The invention can include a one-way fastener in the strip for removably attaching the end cap to the strip. A resilient member and a rigid member can be included in the one-way fastener. In one embodiment the resilient member can be generally conical in shape.

The invention can include a housing affixed to a strip; a hook opening defined in the strip configured to allow the strip hand from a hook such as on an IV pole; a discontinuous area configured to allow multiple strips to be connected to each other forming a chain of strips; an open end defined in the housing; an end cap received in the open end of the housing and releasably attached to the strip; a housing sloped portion defined on an inner wall of the housing; an end cap sloped portion cooperatively associated with the housing sloped portion so that when a proximal end of an IV tube is attached to the end cap, the proximal end cannot be removed from the end cap without removing the end cap from the strip; a resilient member carried by the strip configured to receive a fastening member included in the end cap; a tab removably attached to the open end of the housing configured to cover the housing prior to the proximal end of the IV tube being received by the housing; a sterilization pad included in a control opening defined in the end cap carrying a sterilization agent; and, a circumferential flange included in the end cap configured to engage with the proximal end of the IV tube securing the end cap to the proximal end.

The resilient member can include a rigid ring and a resilient ring. The fastening member can extend through the strip. A portion of the fastening member that extends through the strip can be received into a second fastening member. The fastening member can be a ball and socket arrangement. The control opening can receive a male portion of the proximal end of the IV tube. The end cap can be configured to rotate within the housing.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 7 is a perspective view of the rear and front panel;

FIG. 8A is a cut away view of the end cap and rear panel;

FIG. 8B is a cut away view of the end cap and rear panel;

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Figure 1:
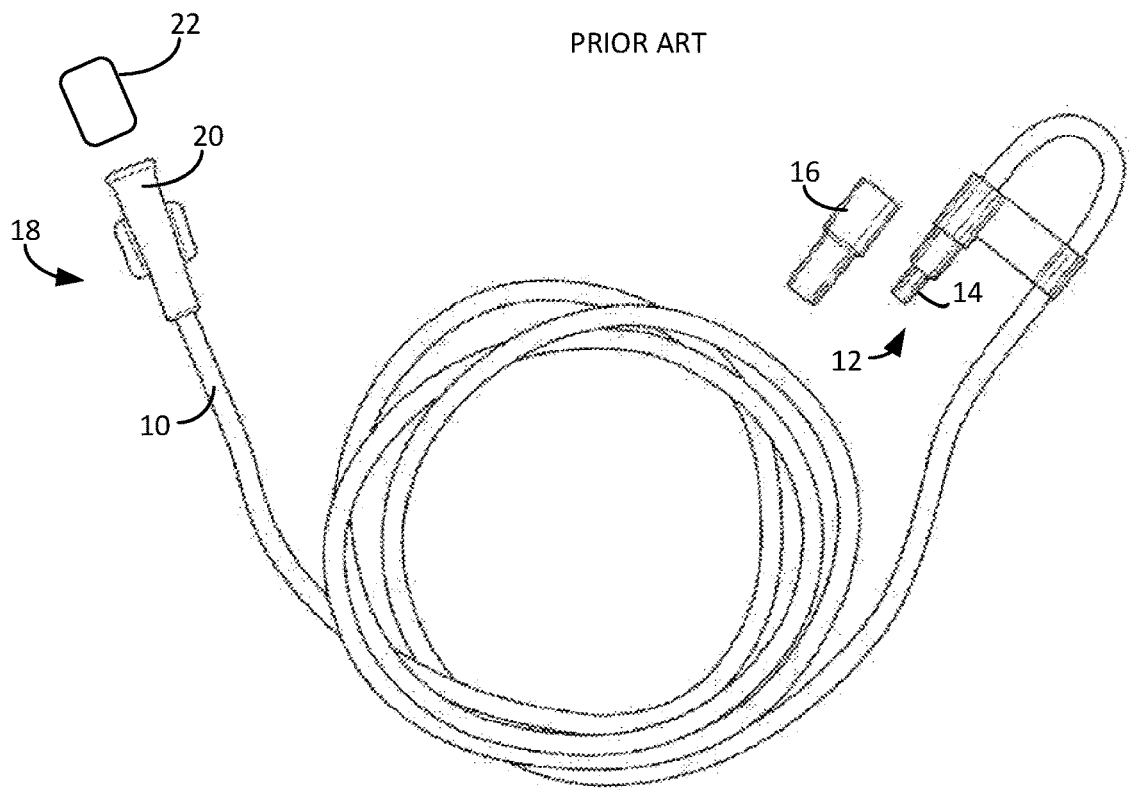
FIG. 1 is a view of an IV-line as is known in the art.

Referring to FIG. 1, an IV-line 10 can include a distal end 12 that includes a male end 14. The male end can be a male luer end. The distal end can be attached to a female end of an IV catheter extension that then would connect to a needle and cannula that is inserted into the patient with a portion of the distal end of the tubing possibly taped to the patient near the insertion site. A distal (male) end cap 16 can be used to cap the distal end of the IV tube. An IV-line end 18 can be included in the IV tube and can include a female end 20. An end cap 22 can be attached to the proximal (female) end. In use, the proximal end is connected to any number of articles including IV medication through the use of other IV connectors. Other female ends, or ports such as the female end 20 can extend from any portion of the tubing of IV-line 10 to create an access point for medication administration through the IV-line. It is the male end 14 that is normally subject to reduced sterility when it is disconnected from the patient without being capped, capped incorrectly, falling to the floor, or with other exposure and the like. When the IV is attached to the end cap and the end cap is attached to the strip, the IV tube can hang from the end cap and therefore does not contact the floor. This feature can prevent the IV tube from being contaminated as well as prevent tangling of the tubes themselves.

Figure 2:
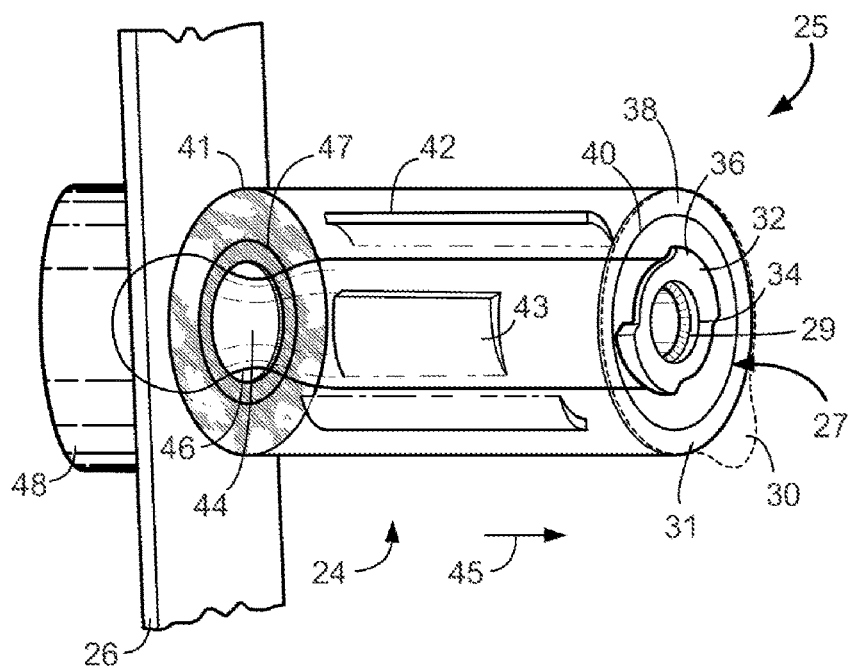
FIG. 2 is a perspective view of the end cap, strip, and housing.

Referring to FIG. 2, an assembly 24 can be attached to a strip 26. In one embodiment, the strip hangs from the IV stand for quicker availability for a nurse. The strip allows an end cap 32 that can be received in a housing 38 that can be affixed to strip. The open end 25 of the housing can have a tear away cover 31 with a tab 30. By providing the tear away cover, the open end of the housing and end cap is covered and sealed to help insure sterility until the nurse is ready to use the cap. The end cap 32 can include a central opening 34 and end cap circumferential flanges 36 that can completely or partially surround the central opening. The central opening can include a sterilization pad or swab 29 attached to the interior of the central opening so that when the end of the IV tube is received in the central opening, the end of the IV tube is sterilized with a sterilization agent.

A swivel portion of an end of an IV tube can be received into the opening 27 defined between the housing 38 and the end cap 32. In one embodiment, the swivel portion of the male end of an IV tube can be received into the housing. The male portion 21 (FIG. 5) would be received into the central opening 34 of the end cap. The inner wall 40 of the housing can include a housing sloped portion 42 that cooperates with an end cap rotation stop 43 disposed on the outer surface of the end cap. The housing sloped portion and the end cap sloped portion can be configured to prevent rotation of the end cap in the housing in one direction and allow rotation in the other direction. Therefore, once the IV connector is attached to the end cap in the housing, the IV tube cannot be removed from the end cap without the end cap being removed from the strip. The IV connector can be disposed so that when attached to the end cap, the swivel portion does not extend into the area occupied by the housing sloped portion 42 in one embodiment.

The end cap can include a first fastening member 44 that can be received into the opening 46 in the strip. In one embodiment the diameter of the first fastening member is larger than the opening so that sufficient force is required to deform the opening to cause the end cap to be removed from the strip. The opening can be defined in the strip or in a second fastening member 48. The first fastening member can extend through the strip and be received into the second fastening member so that the end cap is secured to the strip. In one embodiment, once the end cap is removed from the second fastening member, the second fastening member cannot be replaced preventing reuse of the end cap and promoting compliance with proper IV procedures. In one embodiment, the first fastening member and second fastening member are a ball and socket assembly. In one embodiment, when the end cap is removed from the strip, the housing remains attached to the strip. In one embodiment, the housing is attached to the strip and surrounds the end cap so that when the IV tube is attached to the end cap, the IV tube cannot be separated from the end cap without the end cap being removed from inside the housing. In one embodiment, the housing cannot be removed from the strip. In one embodiment, the second fastening member is not attached to the strip and held in place when the end cap is in place. The second fastening member drops away when the end cap is removed.

In one embodiment, a one-way fastener is included in the strip allowing the end cap to be removably attached to the strip, but not to be replaced on the strip. A rigid ring 41 can define the opening in the strip for receiving the first fastening member. A resilient member 47 is disposed within the housing and adjacent to the end cap when the end cap is attached to the strip. When the end cap is pulled away from the strip in a direction shown as 45, the resilient member deforms inward allowing the first fastening member to be pulled through the opening and removed from the strip. When the end cap is attempted to be replaced by pushing it in a direction opposite that of 45, the resilient member contacts the rigid member and does not sufficiently deform to allow the first fastening member to be placed through the opening in the strip, thereby preventing the end cap from being reused. The rigid ring 41 can be disposed away from open end 25 in relation to the resilient member 47 in one embodiment.

Figure 3:
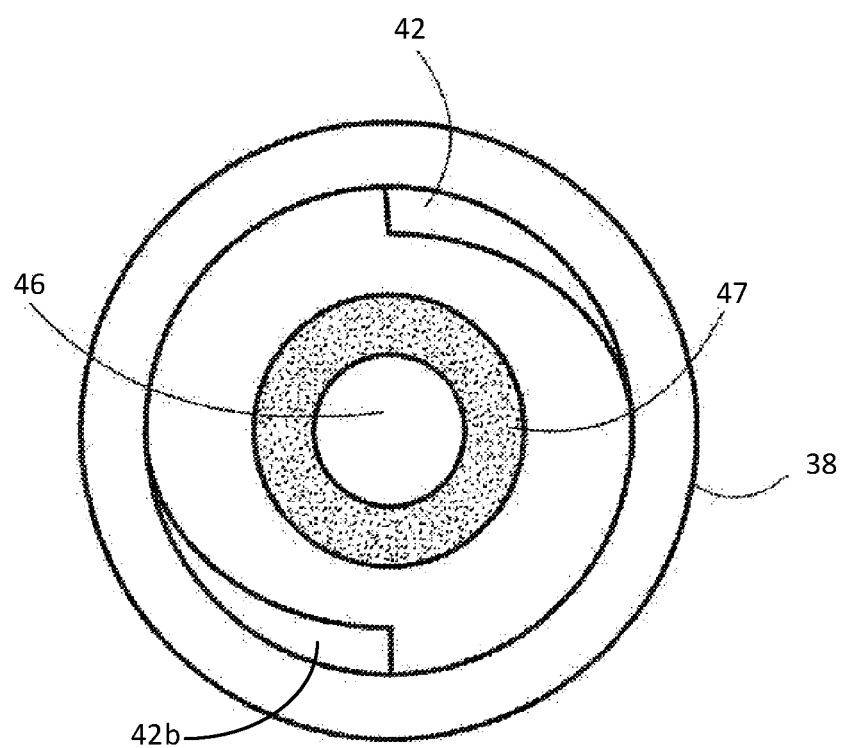
FIG. 3 is an end view of aspects of the housing.

Referring to FIG. 3, the open end of the housing is shown. The opening as shown allows the resilient member 47 to be exposed after the end cap has been removed. The resilient member deforms when the end cap is pulled from the strip. The housing sloped portion 42 can include a second housing sloped member 42b generally on the opposite side of the housing inner wall.

Figure 4:
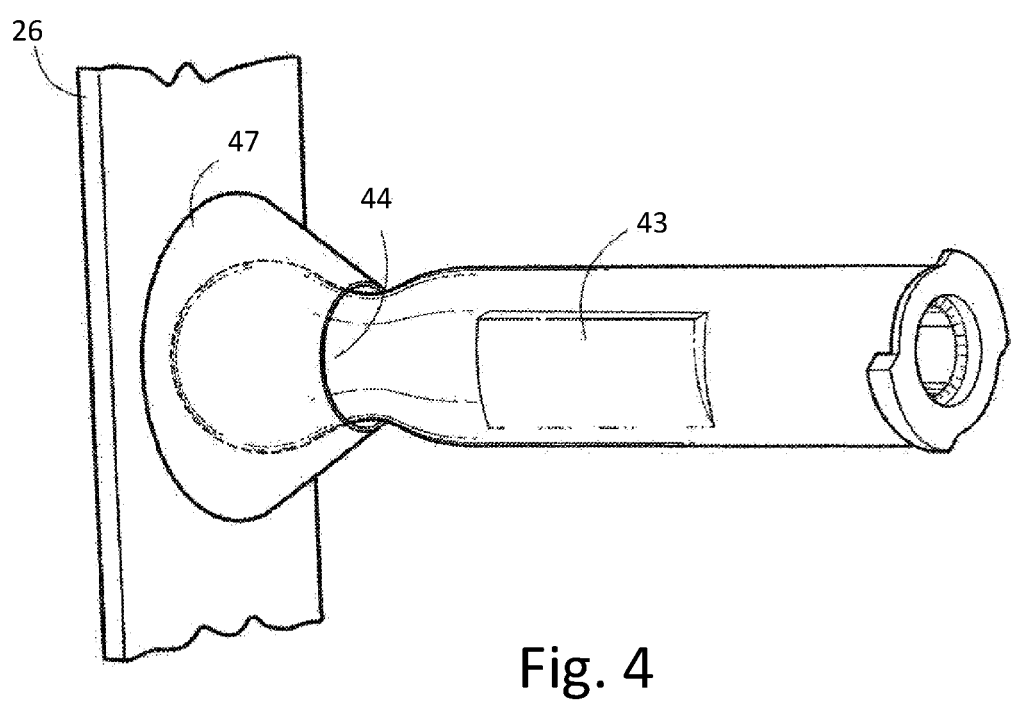
FIG. 4 is a perspective view of aspects of the end cap and strip.

Referring to FIG. 4, the end cap is shown without the housing. The end cap is attached by a first fastening member 44 to a resilient member 47. In this embodiment, the resilient member is attached to the strip 26 so that the first fastening member does not extend through the strip. When the end cap is pulled from the resilient member, the resilient member deforms so that the end cap can be removed. The resilient member reverts generally to its original shape preventing the end cap from being reattached to the strip to deter reuse of the end cap and increase compliance with IV procedures. In one embodiment, the resilient strip is generally a conical shape.

Figure 5:
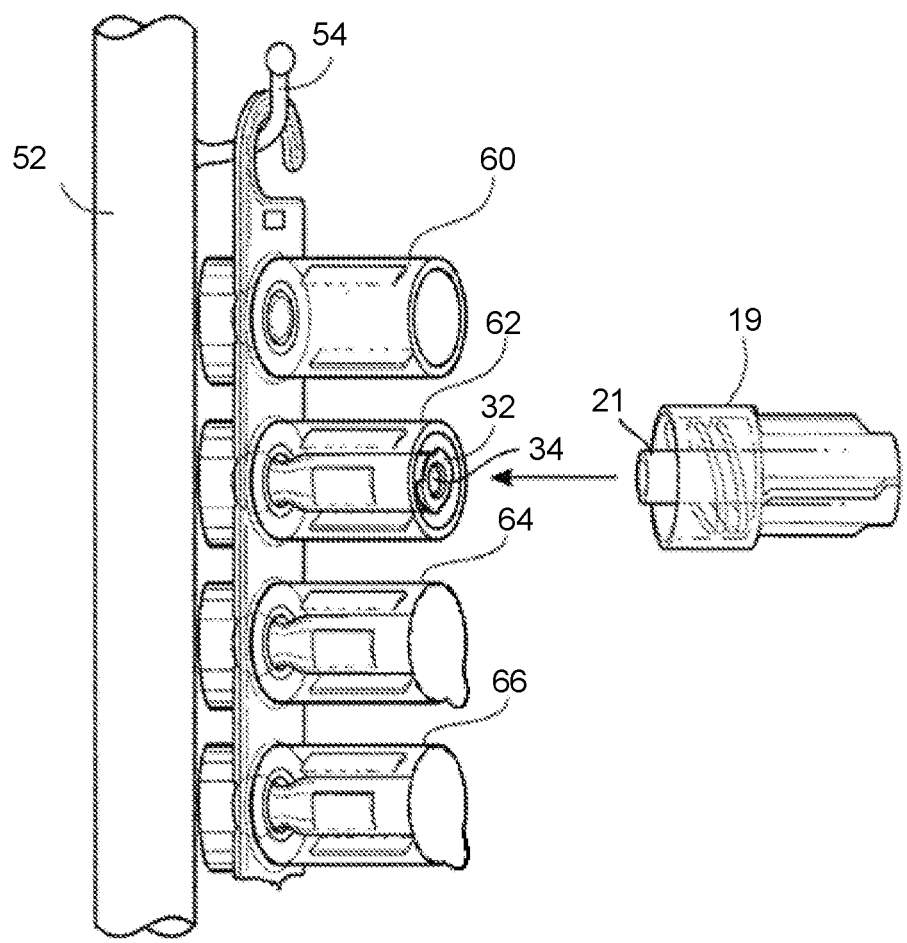
FIG. 5 is a perspective view of the end cap, strip, housing, and IV-line end.

Referring to FIG. 5, the end caps can be positioned on the strip and can hang from an IV stand, pole 52 or wall and can be placed on a hook 54 or another hanging element. The top housing 60 is shown after the end cap has been removed. The next housing 62 is shown with the seal removed and an IV-line end 19 being placed on the end cap. The next housings 64 and 66 are shown with the seals in place and ready for use.

Figure 6A:
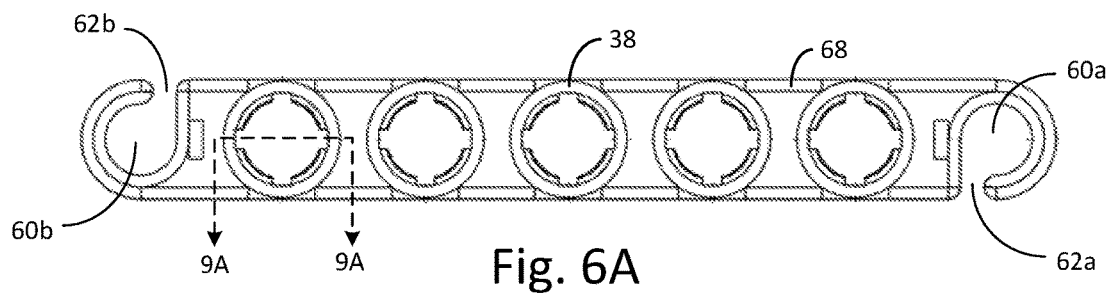
FIG. 6A is a top view of the front panel.
Figure 6B:
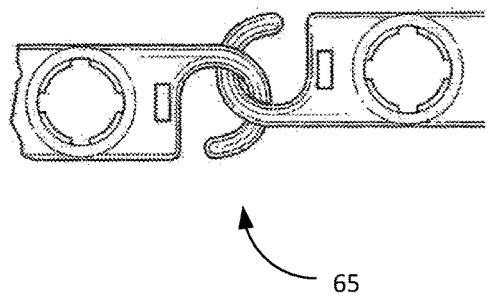
FIG. 6B is a top view of front panels
Figure 6C:
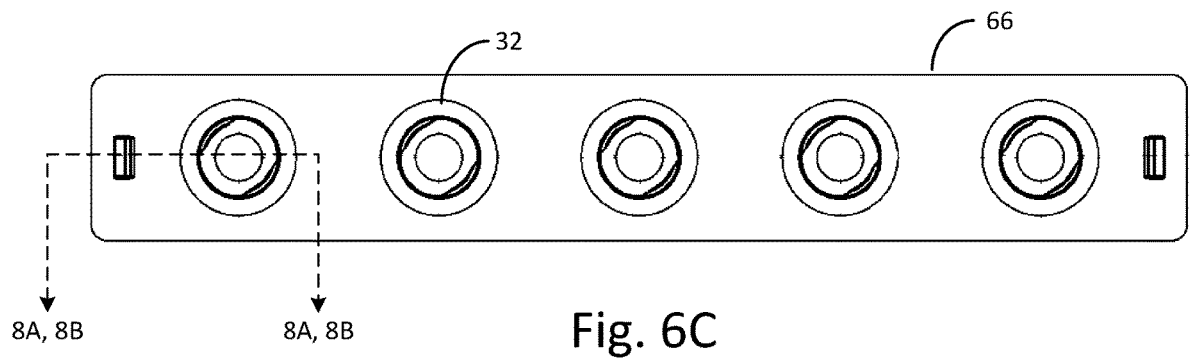
FIG. 6C is a top view of the rear panel.

Referring to FIG. 6A, a front panel 68 can include opening 60 a and 60 b at each end that include discontinuous area 62a and 62b. The discontinuous area can be configured to allow adjacent front panels to be connected to each other in a chain as shown as 65 in FIG. 6B. The front panel can include one or more housings 38 affixed to the front panel. FIG. 6C shows a rear panel 66 having one or more end caps 32 that can be removably attached to the rear panel.

Referring to FIG. 7, the strip can include a rear panel 66 that can include a snap 70. The rear panel can be attached to the front panel 68 and affixed to the front panel when the snap is received into a snap opening 72. The housing 38 can be attached to the front portion. The end cap 32 can be removably attached to the rear portion and received in the housing when the rear panel is attached to the front panel. The end cap can be attached to the rear portion by one or more breakaway connections 74. The break away connections are designed to release from the rear portion when rotational force is placed on the end cap. The rotational force can be applied when an attached IV-line end is twisted.

Referring to FIGS. 8A and 8B, the end cap 32 is attached to the rear panel 66 with lateral breakaway connections 74a and 74b. In one embodiment, when the end cap 32 is attached to the end of an IV-line and the end of the IV-line is twisted, the rotational force causes the end cap 32 to release from the rear panel 66. The end cap can include a base 76 having a larger diameter than the end 78. The base can include a sloped wall 77 between the end 78 and the breakaway connections where the diameter of the base increases from the top of the sloped wall to the portion adjacent the breakaway connections.

Figure 9A:
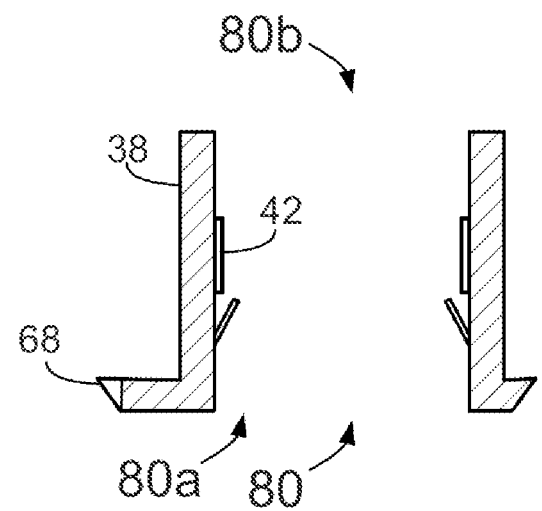
FIG. 9A is a cut away view of the housing and front panel.
Figure 9B:
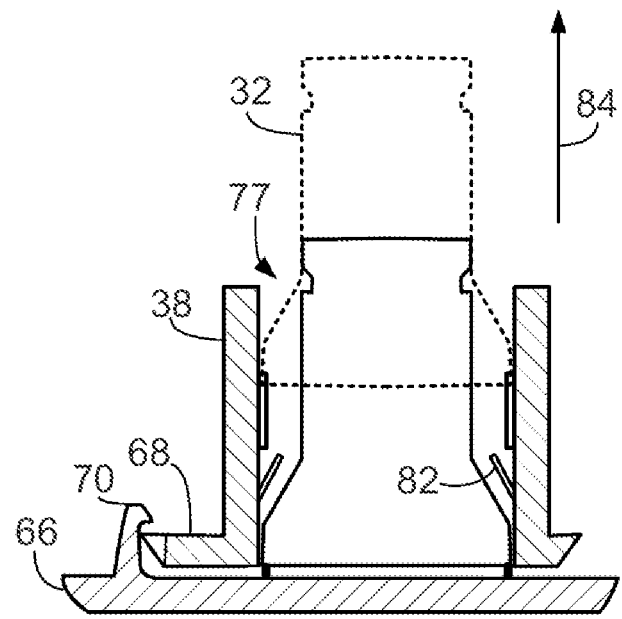
FIG. 9B is a cut away view of the housing and front panel.

Referring to FIGS. 9A and 9B, a cross section of the housing 38 is shown and is attached to the front panel 68. The housing includes an opening or bore 80 that extends through the front panel and the housing and is configured to receive an end cap 32 when the rear panel is attached to the front panel. The bore can include an entry opening 80a and an exit opening 80b.

The housing can include one or more insert stops 82 that can be attached to the interior wall of the housing. The housing stops can be configured to allow the end cap to removed from the housing in a direction 84 so that the case of the end cap travels past the insert stop. The insert stop can prevent the end cap from being reinserted into the housing as the base of the end cap can contact the insert stop preventing the end cap from further traveling in to the housing. Therefore, the end cap can be configured to be a one time use end cap. In one embodiment, the insert stops can deform when contacting the end cap sloped wall 77 to allow the end cap to be removed from the housing. The insert stop can include a flap, ramp, sloped portion, rounded member, or a combination thereof.

Figure 10A:
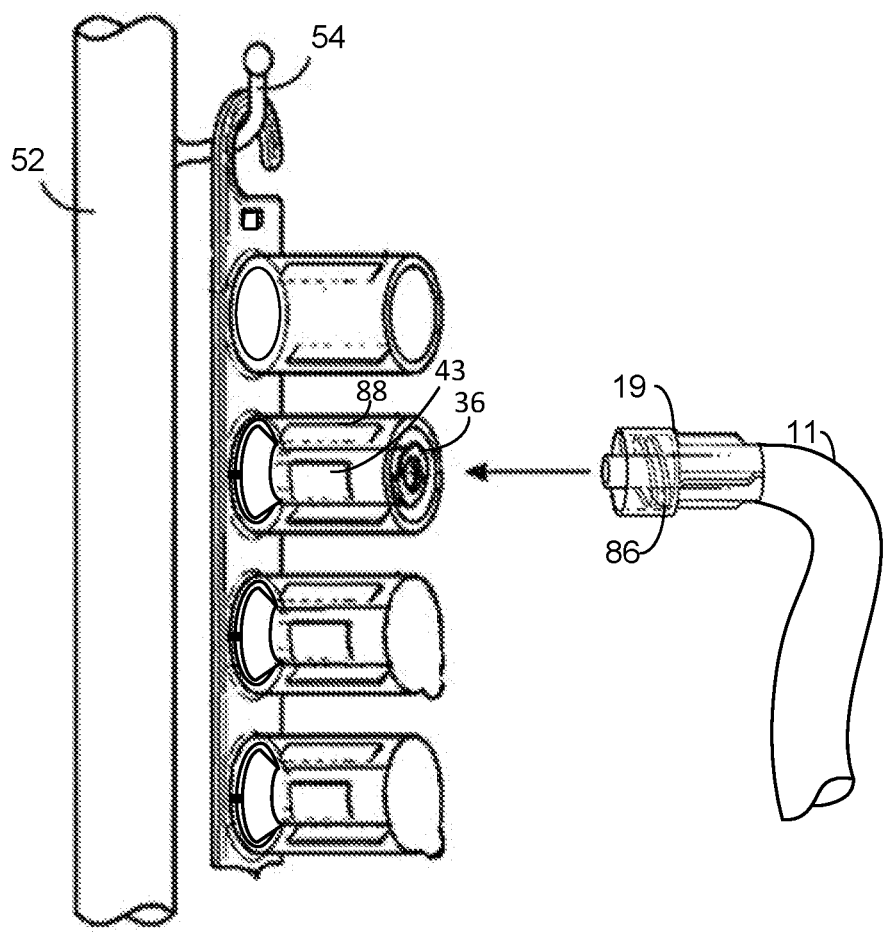
FIG. 10A-10C are perspective views of a pole, end cap, housing, and IV-line end and IV line.
Figure 10B:
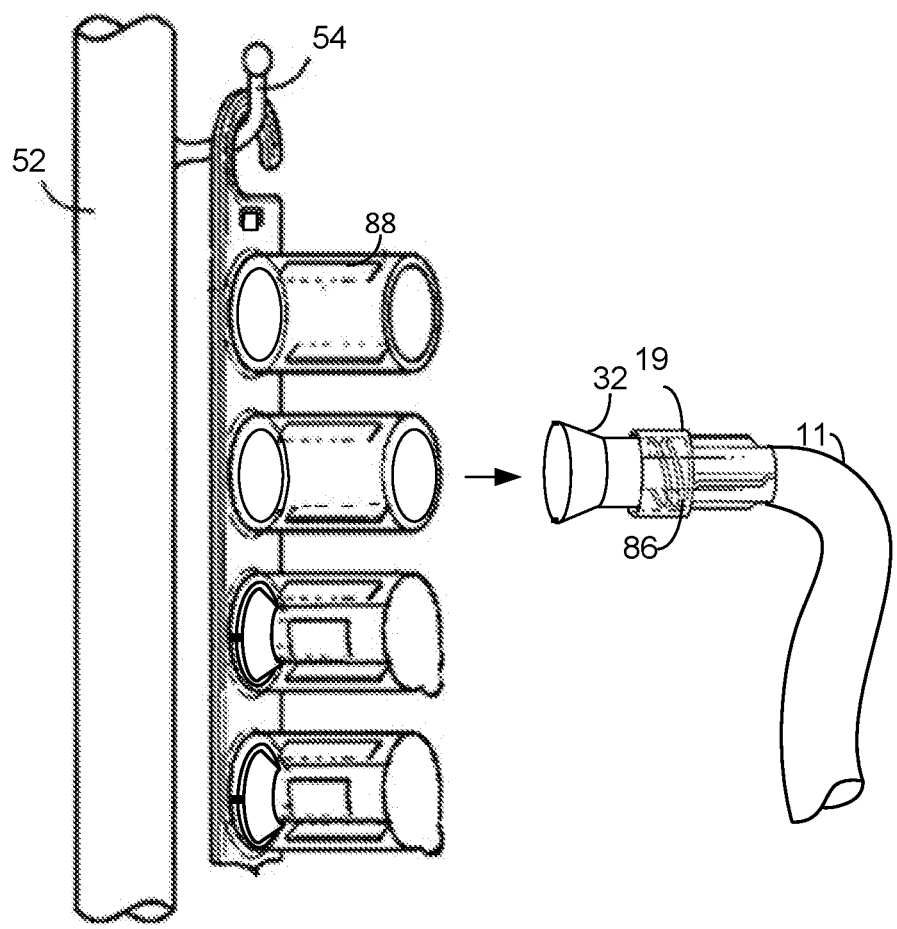
Figure 10C:
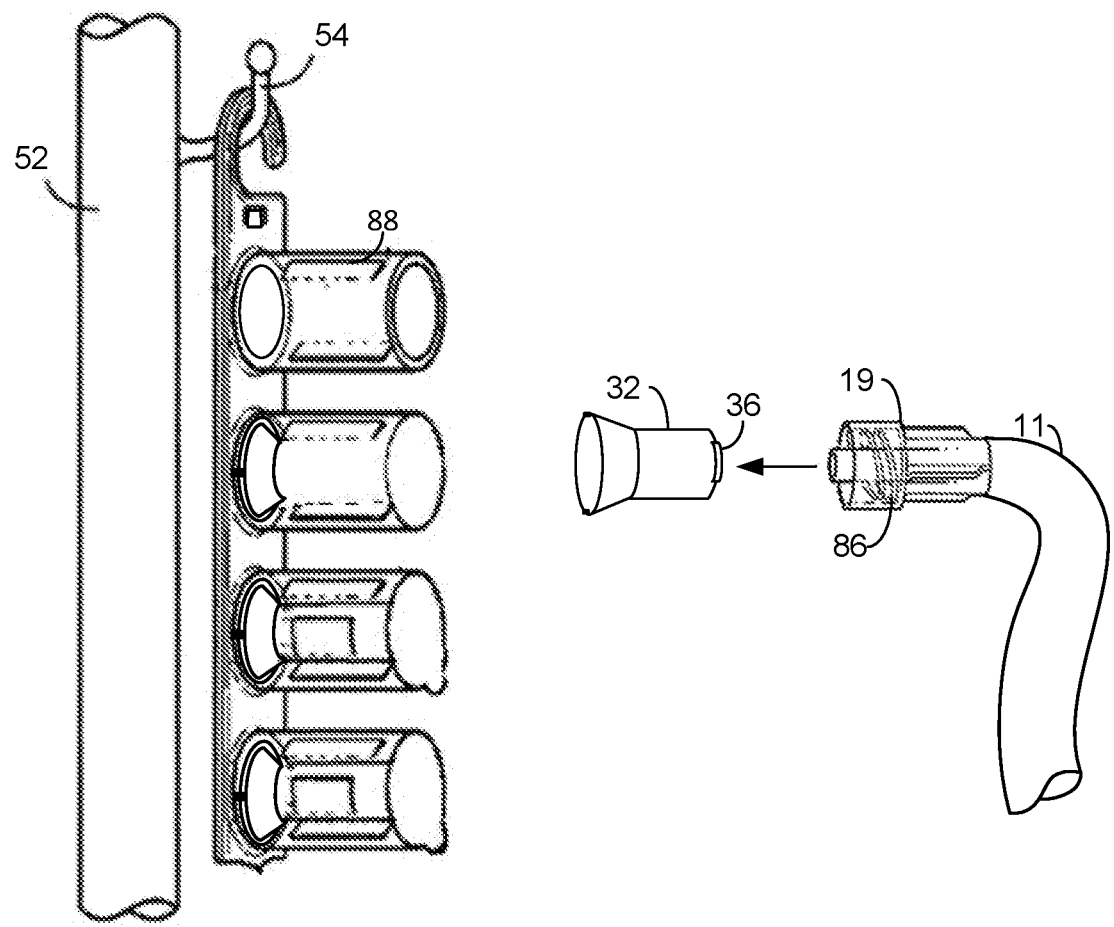

Referring to FIGS. 10A through 10C, the rear panel and the front panel are attached to each other and are supported by pole 52. The IV-line end 19 can be placed on the end cap allowing the IV-line 11 itself to hang away from the pole with the IV line end secured to the end cap in the housing. When the IV-line is connected to the end cap, at least a portion of the IV-line end is disposed on the housing protecting the IV-line end from contact with undesirable surfaces. The IV-line end is secured in a safe location until it is needed for use. The IV-line end threads 86, in one embodiment, are secured to one or more end cap circumferential flange 36. A housing rotational stop 88 can cooperate with an end cap rotation stop 43 so that the end cap does not rotate in one direction allowing the IV-line end to be threaded onto the end cap. In one embodiment, when the IV-line end is continued to be rotated onto the end cap, a breakaway point is reached causing the end cap to release from the rear panel. The end cap then can freely spin in the housing. The end cap, as it is freely spinning in the housing, cannot be removed from the IV-line without pulling the IV-line end and end cap out of the housing.

When the IV-line end and the end cap are pulled form the housing, the base of the end cap is exposed. The base can then be held and rotated so that it can be released from the IV-line end. The based cannot be reinserted into the housing and is therefore discarded providing for a one time use end cap. Once the end cap is removed, the IV-line end can be used normally.

Because the end cap must be detached from the rear panel in order for a nurse to remove the IV-line from the housing and uncap the IV-line, the end of the IV-line is protected, has reduced contamination and reduces the risk of complications with the patient. The end cap portion can cover the central, thin, male catheter portion of the IV-line, and can be removably attached to the rear portion. The end cap is unable to be removed by unscrewing it but must be removed with the end cap being also removed from the rear panel and housing thereby rendering it more difficult to be reused reducing complications and increasing hygiene and sanitation. This functionality increases compliance with IV procedures.

By offering an end cap attached to a strip that is hung from IV poles, nurses are provided with a safer, easier, sterile alternative to the method of "looping" the IV-lines into themselves (found very often among nurses) while offering more ease of use and ready availability of the IV-line for later use. This also allows nurses to more easily organize and identify multiple IV-lines, keeping drugs for more complex patients in order, which will minimize time consumption and mistakes. Not only would hanging stationary IV caps in this manner make it much easier for nurses to comply with hospital regulations, but it would also make them much more willing to do so, which is key in solving the problem of end-user compliance.

These beneficial results are directed to a higher rate of compliance among healthcare providers in charge of intravenous (IV) line care for both central and peripheral lines. Having a higher rate of compliance among providers translates directly to a lower rate of infection, improved patient outcomes, and lower healthcare costs for facilities providing IV care. The end cap can be firmly attached to the strip and cannot be removed without sufficient effort.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. An IV-line end cap and support comprising
a rear panel having an end cap attached to the rear panel by a breakaway connection;
a base included in the end cap having a diameter larger than a diameter of a proximal end of the end cap;
a circumferential flange included in the end cap configured to engage with an IV-line end securing the end cap to the IV-line end;
a front panel attached to the rear panel and having a hook;
a housing attached to the front panel, wherein a bore extends through both the housing and front panel and wherein the housing is configured to receive the end cap through an entry opening of said bore;
wherein the end cap, breakaway connection and housing are configured to allow the end cap to rotate in one direction within the housing after said breakaway connection is severed to prevent the IV-line from being removed from the end cap until the end cap is removed from the housing through an exit opening;
an insert stop included in the housing configured to cooperate with the base of the end cap and prevent the end cap from being fully reinserted into the housing past said insert stop;
a sterilization pad included in a control opening defined in the end cap carrying a sterilization agent and,
a tab removably attached to an open end of the housing configured to cover the housing prior to the IV-line end being attached to the end cap.

2. The support of claim 1 wherein the insert stop is a flap.

3. The support of claim 2 wherein the flap is configured to deform when the end cap is removed from the housing.

4. The support of claim 1 wherein the base of the end cap is disposed below the insert stop when the end cap is disposed in the housing prior to being released from said rear panel.

5. An IV-line end cap and support comprising
a rear panel having an end cap releasably attached to the rear panel;
a base included in the end cap having a diameter larger than a diameter of a proximal end of the end cap;
a circumferential flange included in the end cap configured to engage with an IV-line end securing the end cap to the IV-line end;
a front panel attached to the rear panel, wherein said front panel includes a hook;
a housing attached to the front panel, wherein the housing is configured to receive the end cap;
wherein the end cap and housing are configured to allow the end cap to rotate in one direction within the housing after being released from said rear panel to prevent the end cap from being removed from the IV-line end until the end cap is removed from the housing.

6. The support of claim 5 including an insert stop included in the housing configured to cooperate with the base of the end cap and prevent the end cap from being fully reinserted into the housing past said insert stop.

7. The support of claim 6 wherein the insert stop is a flap.

8. The support of claim 5 including a sterilization pad included in a control opening defined in the end cap carrying a sterilization agent.

9. The support of claim 5 including a tab removably attached to an open end of the housing configured to cover the housing prior to the IV-line end being attached to the end cap.

10. The support of claim 5 where in the housing is configured to receive the end cap through an entry opening and the end cap is released from the rear panel and removed from the housing through an exit opening.

* * * * *